(12) United States Patent
Eckert et al.

(10) Patent No.: US 11,432,732 B2
(45) Date of Patent: Sep. 6, 2022

(54) SYSTEM AND METHOD OF MEASURING MILLIMETER WAVE OF COLD ATMOSPHERIC PRESSURE PLASMA

(71) Applicant: ChiScan Holdings, LLC, Las Vegas, NV (US)

(72) Inventors: Bryon K. Eckert, Chandler, AZ (US); Bradley N. Eckert, Chandler, AZ (US); Huan Truong, Chandler, AZ (US)

(73) Assignee: ChiScan Holdings, LLC, Las Vegas, NV (US)

( * ) Notice: Subject to any disclaimer, the term of this patent is extended or adjusted under 35 U.S.C. 154(b) by 874 days.

(21) Appl. No.: 15/636,554

(22) Filed: Jun. 28, 2017

(65) Prior Publication Data

US 2017/0367613 A1    Dec. 28, 2017

Related U.S. Application Data

(60) Provisional application No. 62/355,537, filed on Jun. 28, 2016.

(51) Int. Cl.
*A61B 5/0507* (2021.01)
*G01R 29/08* (2006.01)
(Continued)

(52) U.S. Cl.
CPC ........ *A61B 5/0507* (2013.01); *A61B 5/14542* (2013.01); *A61B 5/7203* (2013.01);
(Continued)

(58) Field of Classification Search
CPC .................... A61B 5/0507; A61B 2562/0228
See application file for complete search history.

(56) References Cited

U.S. PATENT DOCUMENTS 4,357,709 A * 11/1982 Butler ................. H04K 3/41
342/14
5,115,168 A    5/1992 Shoda et al.
(Continued)

OTHER PUBLICATIONS

Rubinski, "Incremental Encoder Ouput Signal Overview" (Year: 2015).*
(Continued)

*Primary Examiner* — Serkan Akar
*Assistant Examiner* — Aminah Asghar
(74) *Attorney, Agent, or Firm* — Messner Reeves LLP (57) ABSTRACT

A detection device for detecting and characterizing biological energy fields emitted by biological specimens is configured to collect and analyze an electromagnetic signal that includes millimeter-length waves generated by the interaction of atmospheric plasma with torsion waves of the biological energy field. The device performs spectral analysis on the millimeter waves to determine characteristics of the corresponding torsion waves that generated them. An array of several hundred non-thermal plasma plumes are placed directly in front of a circular horn. A switchable circular polarizer is used to select left hand circular, linear or right hand circular polarization. A low noise frequency converter allows a noise temperature of less than 1150 K. A frequency scan and averaging algorithm is developed to characterize noise temperature versus frequency, comparing signal and noise levels between plasma on and plasma off, and switching polarization sense.

14 Claims, 7 Drawing Sheets

(51) Int. Cl.
  *A61B 5/00* (2006.01)
  *H05H 1/24* (2006.01)
  *A61B 5/145* (2006.01)

(52) U.S. Cl.
  CPC ............ *A61B 5/725* (2013.01); *A61B 5/7257* (2013.01); *G01R 29/0814* (2013.01); *G01R 29/0892* (2013.01); *H05H 1/2406* (2013.01); *A61B 2562/0228* (2013.01); *H05H 1/245* (2021.05)

(56) References Cited

U.S. PATENT DOCUMENTS

| | | | |
|---|---|---|---|
| 5,130,003 | A | 7/1992 | Conrad |
| 5,363,054 | A | 11/1994 | Bekefi |
| 5,705,931 | A | 1/1998 | Klick |
| 5,909,086 | A | 6/1999 | Kim et al. |
| 6,713,965 | B2 | 3/2004 | Jang et al. |
| 7,564,419 | B1 * | 7/2009 | Patel ................... H01Q 15/244 343/756 |
| 8,460,283 | B1 | 6/2013 | Laroussi et al. |
| 2004/0135590 | A1 | 7/2004 | Quon |
| 2005/0116871 | A1 * | 6/2005 | Moheb ............... H01Q 13/0258 343/772 |
| 2008/0097183 | A1 * | 4/2008 | Monro .................... A61B 5/01 600/407 |
| 2009/0292196 | A1 * | 11/2009 | Eckert .................... A61B 5/05 600/407 |
| 2010/0296977 | A1 | 11/2010 | Hancock |
| 2011/0109519 | A1 * | 5/2011 | Quan ................. H01Q 15/0006 343/756 |
| 2011/0118556 | A1 | 5/2011 | Siegel et al. |
| 2012/0156093 | A1 | 6/2012 | Kitano |
| 2012/0309328 | A1 * | 12/2012 | Morrison ............... H04B 1/525 455/78 |
| 2014/0263202 | A1 | 9/2014 | Partridge |
| 2014/0309522 | A1 * | 10/2014 | Fullerton ............... A61B 5/064 600/424 |
| 2014/0319382 | A1 | 10/2014 | Hancock et al. |
| 2015/0056107 | A1 | 2/2015 | Hancock |
| 2016/0065256 | A1 * | 3/2016 | Yun ...................... H04B 1/1027 375/349 |
| 2016/0317061 | A1 * | 11/2016 | Ostadrahimi ........ A61B 5/0507 |
| 2016/0337986 | A1 * | 11/2016 | Broda ................... H04H 20/59 |
| 2021/0068896 | A1 | 3/2021 | Eckert et al. |

OTHER PUBLICATIONS

Ibrahim et al., "Performance Analysis of Fast Fourier Transform on Field Programmable Gate Arrays and Graphic Cards" (Year: 2016).*

Sathasivam et al., "ASIC Implementation of High throughput FFT Processor for Scientific Applications" (Year: 2016).*

Nie et al.m "A two-dimensional cold atmospheric plasma jet array for uniform treatment of large-area surfaces for plasma medicine", New Journal of Physics, vol. 11 (Year: 2009).*

Rubinski, "Incremental Encoder Ouput Signal Overview", wayback machine document (Year: 2015).*

Arata Y., et al., "Contribution of Higher Harmonic Resonance on the Production of ECR Mirror Plasma by 60 GHz Gyrotron," Japanese Journal of Applied Physics, Feb. 1989, vol. 28(2), pp. 234-239.

Jackson G.L., et al., "Second Harmonic Electron Cyclotron Pre-Ionization in the DIII-D Tokamak," Nuclear Fusion, Mar. 19, 2007, vol. 47, pp. 257-263.

Kamoda H., et al., "Millimeter-Wave Beam Former Using Liquid Crystal," 34th European Microwave Conference, 2004, pp. 1141-1144.

Schmuck S., et al., "Electron Cyclotron Emission Spectra in X- and O-Mode Polarisation at JET: Martin-Puplett Interferometer, Absolute Calibration, Revised Uncertainties, Inboard/Outboard Temperature Profile, and Wall Properties," Review of Scientific Instruments, 2016, vol. 87(9), pp. 1-25.

Udintsev., V.S., et al., "New ECE Diagnostics for the TEXTOR-94 Tokamak," Review of Scientific Instruments, Jan. 3, 2001, vol. 72 (1), pp. 359-362.

Wiltse J.C., "History of Millimeter and Submillimeter Waves," IEEE Transactions on Microwave Theory and Techniques, Sep. 9, 1984, vol. 32 (9), 10 pages.

* cited by examiner

SYSTEM AND METHOD OF MEASURING MILLIMETER WAVE OF COLD ATMOSPHERIC PRESSURE PLASMA

CROSS-REFERENCE TO RELATED APPLICATIONS

This application is a nonprovisional claiming the benefit of priority of U.S. Prov. Pat. App. Ser. No. 62/355,537, filed Jun. 28, 2016, under the title "Novel Technique of Measuring Millimeter Wave of Cold Atmospheric Plasma," the entirety of which is incorporated fully herein by reference.

FIELD OF INVENTION

This disclosure relates to millimeter wave detection. In particular this disclosure relates to methods and devices for detecting and analyzing energy fields emitted by organisms.

BACKGROUND

All live organisms emit energy biofields in the form of waves, which are characterized by the organic processes that produce or modify them. There is a significant difficulty in detecting, measuring, and describing the energy in these biofields, inhibiting human understanding of biological interactions with the environment. Energy waves emanating from a live organism are often referred to as torsion waves, and are analogous to electromagnetic waves. Plasma arrays placed next to the skin of an organism can induce torsion waves emanating from a body to be converted to electromagnetic waves, which can be more directly measured and analyzed using millimeter-wave electronics.

Plasma is an ionized state of matter known for its cleaning, decontaminating, sterilizing, antimicrobial and healing properties when applied to an inanimate surface or to tissue. Plasma can be created when energy is applied to a substance. As energy input is increased, the state of matter changes from solid, to liquid, to a gaseous state. If additional energy is fed into the gaseous state, the atoms or molecules in the gas will ionize and change into the energy rich plasma state, or the fourth fundamental state of matter.

There are two types of plasma, thermal and non-thermal, which is also known as cold plasma. Thermal plasmas are in thermal equilibrium, i.e. the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges. If thermal plasma is used in treating a material or surface sensitive to heat, it can cause significant thermal desiccation, burning, scarring and other damage.

In order to mitigate such damage, methods and devices have been created for applying non-thermal plasma to heat-sensitive materials and surfaces. Whereas in thermal plasmas the heavy particles and electrons are in thermal equilibrium with each other, in non-thermal plasmas the ions and neutrals are at a much lower temperature (sometimes as low as room temperature) than the electrons. Non-thermal plasma usually can operate at less than 104° F. at the point of contact. Thus non-thermal plasmas are not likely to damage human tissue. Recent research has shown that non-thermal plasmas may have a number of beneficial medical effects, such as the treatment of localized infections, though the underlying mechanism of non-thermal plasma therapy is not fully understood. The beneficial health effects of non-thermal plasma applications in living organisms are often attributed to reactive oxygen or nitrogen species.

An unexplained repulsive force that is occasionally observed during non-thermal plasma treatment of infections may point the way to an efficient mechanism for characterizing biofield energy. Ambient pressure air plasma in non-thermal equilibrium creates localized areas where a population of atoms or molecules are induced to a higher state of excitability, known as population inversion, causing spontaneous emission at magnetic dipole rotational resonance lines. For $O_2$, many of these lines occur in the 60 GHz frequency range.

Extremely high-frequency (EHF) therapy is the practice of using low-intensity electromagnetic radiation in the millimeter band for the treatment of internal disorders, such as various types of cancer and tumors. Recently a possible link between the fine resonance frequencies of oxygen in the 60 GHz region and the therapeutic frequencies used in non-thermal EHF therapy has been investigated. This link could be characteristic of biological torsion fields, and provide additional insight regarding the therapeutic mechanisms of plasma medicine.

SUMMARY

The present device utilizes a system for detecting and measuring millimeter-wave output from a plasma array for biological torsion field characterization. The device for detecting and characterizing biofields, the device comprises a microwave horn positioned to receive radio carrier wave signals generated at an interface between a biological specimen and a plasma array generating atmospheric pressure plasma. The microwave horn concentrates the radio carrier wave signals to produce a concentrated radio signal. A switchable polarizer in communication with the microwave horn and receives the concentrated radio signal. The polarizer selectably applies one of a linear polarization, a left-hand circular polarization, and a right-hand circular polarization to the concentrated radio signal to produce a polarized millimeter wave signal. A programmable frequency converter in communication with the polarizer and comprises a millimeter-wave spectrum receiver module that receives polarized signal as input and produces sliding intermediate frequency I/Q signals as output. A quadrature coupler is in communication with the millimeter wave spectrum receiver module, the coupler receives the sliding intermediate frequency I/Q signals and combines the sliding intermediate frequency I/Q signals to produce a high sideband intermediate frequency and a low sideband intermediate frequency. A sideband select switch in communication with the quadrature coupler and configured to receive the high sideband intermediate frequency and the low sideband intermediate frequency and to output a down-sampled intermediate frequency signal. It selectably comprises the high sideband intermediate frequency or the low sideband intermediate frequency.

A spectrum analyzer in communication with the programmable frequency converter and receiving a down-sampled intermediate frequency signal and produces digital output data comprising a frequency spectrum analysis of the down-sampled intermediate frequency signal. The millimeter wave receiver module comprises a first local oscillator generating a first reference signal at a first frequency, a first mixer in communication with the first local oscillator and receiving the first reference signal, the first mixer combining the first reference signal with the polarized signal to produce a first intermediate frequency signal. A low noise amplifier in communication with the first mixer filters unwanted image frequencies from the first intermediate frequency signal to produce a filtered first intermediate frequency signal.

A second local oscillator generates a second reference signal at a second frequency and a second mixer in communication with the low noise amplifier and the second local oscillator mixes the filtered first intermediate frequency signal with the second reference signal to produce sliding intermediate frequency I/Q signals, an inherent (I) output and a quadrature (Q) output, with the phase of the I and Q outputs differing by 90 degrees.

The spectrum analyzer comprises an analog filter elements configured to receive down-sampled intermediate frequency signals and produce a filtered down-sampled intermediate frequency signal, wherein the filter elements remove unwanted frequency components of the down-sampled intermediate frequency signal. An analog-to-digital converter (ADC) configured to convert the filtered down-sampled intermediate frequency signal to a digital signal, wherein the sampling frequency of the ADC is greater than the first frequency of the first local oscillator and greater than the second frequency of the second local oscillator. A dynamic random access memory (DRAM) module in communication with the ADC, is configured to store the digital signal. Hardware configured to receive the digital signal and perform fast Fourier transform analysis on the digital signal. The detector is configured to receive millimeter wave radio signals in a frequency range corresponding to the resonant frequencies of oxygen. The switchable polarizer is configured to be electronically switched between applying the linear polarization, the left-hand circular polarization, and the right-hand circular polarization to the concentrated radio signal. The programmable frequency converter includes a low pass filter to remove unwanted frequencies below a threshold frequency. The spectrum analyzer includes a notch filter to remove specific frequencies from the down-sampled intermediate frequency signal. The spectrum analyzer includes a saw filter to remove specific frequencies from the down-sampled intermediate frequency signal. The spectrum analyzer includes a local oscillator and mixer, wherein the local oscillator is configured to generate a reference signal at a specified frequency band, and the mixer combines the references signal and the down-sampled intermediate frequency signal to modulate the frequency of the down-sampled intermediate frequency signal. The spectrum analyzer includes FFT analysis hardware implemented in a field programmable gate array. The spectrum analyzer includes FFT analysis hardware implemented in an application specific integrated circuit.

The device includes an antenna capable of receiving millimeter wave radio signals generated from a biofield of a biological organism. It also includes a switchable polarizer in communication with the antenna, the polarizer configured to selectably apply one of a linear polarization, a left-hand circular polarization, and a right-hand circular polarization to the millimeter wave radio signals. A programmable frequency converter is in communication with the switchable polarizer, the frequency converter is configured to receive polarized millimeter wave signals of a first frequency and modulate the received signals to produce modulated signals at a second frequency, and a spectrum analyzer is in communication with the programmable frequency converter. The spectrum analyzer is configured to produce digital output data comprising a frequency spectrum analysis of the modulated signals, the digital output data identifying the millimeter wave radio signals. The digital output data is a set of correlated FFT results. The programmable frequency converter includes a local oscillator generating a reference signal at a first frequency. A harmonic mixer in communication with the local oscillator and receiving the reference signal, the mixer producing an intermediate frequency signal by combining the reference signal with the polarized millimeter wave signals.

A wideband low noise amplifier in communication with the harmonic mixer and filtering any unwanted image frequencies from the first intermediate frequency signal. The spectrum analyzer includes a high speed analog-to-digital converter (ADC) with a sampling rate higher than the sampling rate of a local oscillator that converts analog millimeter wave signals to a digital signal. Dynamic random access memory (DRAM) in communication with the ADC, the DRAM configured to store bursts of digital data. A digital down-converter configured to modulate the frequency of digital signals and fast Fourier transform analysis hardware is implemented in a field programmable gate array. The fast Fourier transform analysis hardware is implemented in an application specific integrated circuit.

A method of analyzing multiple radio signals and detecting a biofield torsion wave signal, that includes placing a non-thermal plasma array near a surface of a biological organism such that plasma generated by the plasma array interacts with biofield torsion waves emitted at the surface to produce high frequency millimeter wave radio signals. It includes receiving the millimeter wave radio signals with a detector, wherein receiving millimeter wave radio signals comprises positioning a microwave antenna of the detector to receive radio carrier wave signals generated at an interface between the surface of the biological specimen and the plasma array, causing the detector to produce, from the radio carrier wave signals, a digital output identifying the millimeter wave radio signals. It includes causing the detector to produce the frequency spectrum analysis that comprises utilizing the microwave horn to concentrate the radio carrier wave signals to produce a concentrated radio signal. It includes selectably applying one of a linear polarization, a left-hand circular polarization, and a right-hand circular polarization to the concentrated radio signal to produce a polarized millimeter wave signal with a switchable polarizer. It includes converting the polarized millimeter wave signals to a down-sampled intermediate frequency signal. The conversion process comprises receiving polarized millimeter wave signals with a millimeter-wave spectrum receiver module and producing sliding intermediate frequency I/Q signals as output. It includes receiving sliding intermediate frequency I/Q signals with a quadrature coupler. It includes combining the signals into a first mixing product and a second mixing product, wherein the first mixing product is a high sideband intermediate frequency and the second mixing product is a low sideband intermediate frequency. It includes selecting to receive a high sideband intermediate frequency or a low sideband intermediate frequency. It includes passing a down-sampled intermediate frequency signal. It includes receiving a down-sampled intermediate frequency signal and producing the digital output. The method includes converting the polarized millimeter wave signals to a down-sampled intermediate frequency signal. It includes generating a first reference signal at a first frequency by a first local oscillator, wherein the first frequency may be multiplied by a first value to modulate the frequency of the reference signal. It includes producing a first intermediate frequency signal by combing the first reference signal with a polarized millimeter wave signal. It includes filtering any unwanted image frequencies from the first intermediate frequency signal. It includes generating a second reference signal at a second frequency by a second local oscillator, wherein the second frequency may be multiplied by a second value to modulate the frequency of the second reference signal. It includes producing two sliding intermediate frequency outputs by combining the second reference signal with the first intermediate frequency signal, wherein the first output is an inherent (I) output and the second output is a quadrature (Q) output and the phase of the I and Q outputs differ by 90 degrees. The method includes producing a digital output that comprises receiving down-sampled intermediate frequency signals, filtering unwanted frequency components of the down-sampled intermediate frequency signal; converting the filtered down-sampled intermediate frequency signal to a digital signal, storing the digital signal in a dynamic random access memory (DRAM) module, and performing fast Fourier transform analysis on the digital signal.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

A wave in an energy field is considered to be composed of electric, magnetic, gravitational and temporal components. The electric, magnetic, and gravitational components are orthogonal to each other. In an electromagnetic wave, the gravitational and temporal components have a static value, and the electric and magnetic components dynamically vary with an inverse relationship. In this context, a static temporal component equates to time moving forward at a constant rate. In contrast, biofield energy emitted as waves is theorized to contain static electric and magnetic components and dynamic temporal and gravitational components. Such a wave is essentially a longitudinal or compression wave in the space-time fabric, but is often referred to as a torsion wave. Time and gravitation components of a torsion wave serve as analogous counterparts to the electric and magnetic components of a transverse electromagnetic wave. Biofield energy is thought to be involved in the regulation of biochemical, cellular, and neurological processes that arise from electromagnetic and quantum field activity.

Extremely high frequency (EHF) electromagnetic waves, with frequencies in the 30-300 GHz range, are referred to as millimeter-waves due to the size of their wavelengths. This frequency band is commonly used across a range of research and technology applications including radio astronomy, telecommunications, security scanners at airports, and even weapon systems. Millimeter waves have also been used in biology and medicine, often known as EHF therapy, for the treatment of a number of diseases. In these therapies, electromagnetic radiation of low power but extremely high frequency is applied to bodily areas. Power levels range from 1 $pW/cm^2$ to 10 $mW/cm^2$, and biological effects are weakly related to power level. Applying EHF electromagnetic waves to the body have been observed to modulate immune response, reduce local pain, or even have positive effects on the treatment of cancer. Some common therapeutic frequencies are 53.6 GHz and 61.2 GHz. These correspond to some of the fine resonance frequencies of oxygen, which are centered around 60 GHz at atmospheric pressure. Typically, a cavity-stabilized Gunn or impact ionization avalanche transition-time diode (IMPATT) oscillator is used as a signal source in EHF therapy, such the frequency may be modulated over a 10 MHz bandwidth to ensure the source frequency sweeps over therapeutic frequency range.

Another area of research that is gaining attention is plasma medicine. Plasmas are a fourth state of matter that are created when energy is applied to a substance. They are typically formed when a gas is subjected to high stresses that create a mixture of neutral atoms, positively charged atomic and molecular ions, and freed electrons. There are two types of plasma, thermal and non-thermal, the latter of which is also known as cold plasma. Thermal plasmas are in thermal equilibrium, i.e. the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges, and is not appropriate for treating material sensitive to heat because it can cause significant thermal desiccation, burning, scarring and other damage.

Non-thermal plasmas occur when the electrons are in much more energetic state than the neutral or positively charged particles. The application of non-thermal plasma in medicine has recently been a fruitful field of research. Numerous published papers have noted biological effects based on the modulation frequency of non-thermal air plasma. The beneficial health effects of non-thermal plasma applications in living organisms are often attributed to reactive oxygen or nitrogen species. Closer investigation of the health effects imparted by an array of micro-plasmas placed near the skin shows energetic effects that are not explained by conventional science.

Figure 1A:
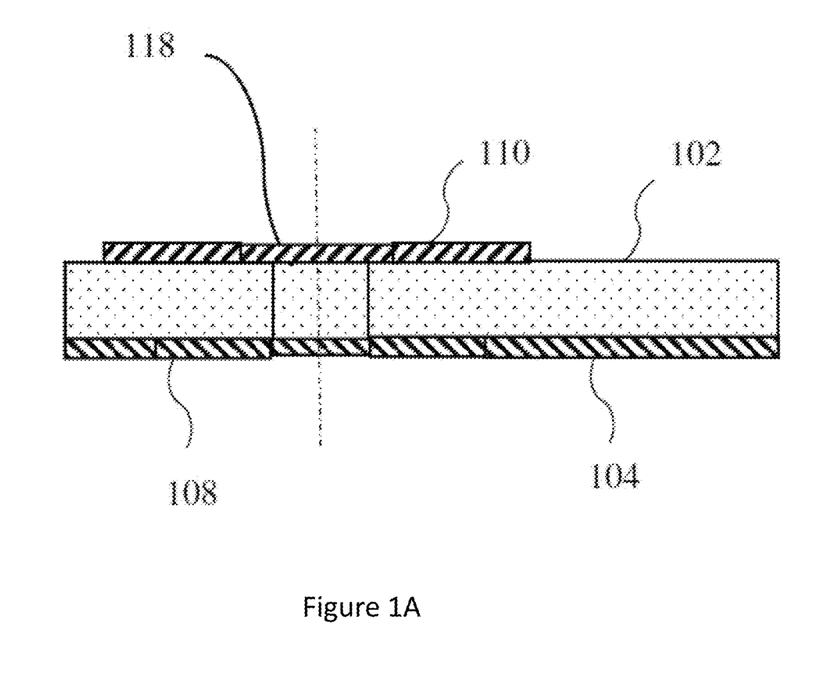
FIG. 1a is an illustration of side view of a plasma array.
Figure 1B:
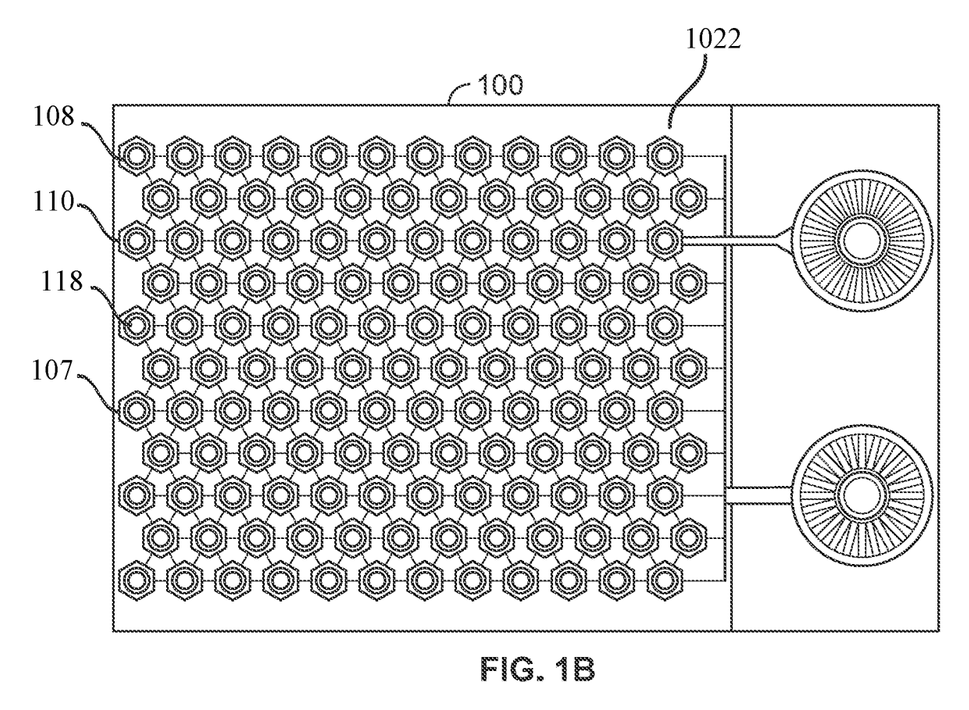
FIG. 1b is an illustration of a top view of a plasma array.

One application of plasma therapies utilizes an array of non-thermal air plasma plumes. An example of such an array is shown in FIGS. 1A and 1B. The example array 100 comprises a substrate 102 having at least two opposing surfaces, referred to herein sometimes as a top and bottom for convenience. A plurality of through-holes 118 are made in the substrate 102. A plurality of drive electrodes 110 are placed on the top of the substrate 102, with each drive electrode 110 centered over one through-hole 118 in the substrate 102. A plurality of ground electrodes 108 is placed on the bottom of the substrate 102, with each ground electrode 108 centered over one through-hole 118 in the substrate 102. The resulting structure of a through-hole 118, a ground electrode 108, and a drive electrode 110 comprises a plasma emitter 107.

To create non-thermal plasma, a potential gradient is applied between two electrodes (e.g., the ground electrode 108 and the drive electrode 110 of a plasma emitter 107); one electrode (the high voltage electrode, e.g., the drive electrode 110) may be subjected to an electric current, while the other electrode is electrically grounded. Typically the electrodes are in an environment of a fluid such as helium, nitrogen, heliox, argon, or air. When the potential gradient between the high voltage electrode and grounded electrode is large enough, the fluid between the electrodes ionizes and becomes conductive. The ionization of the gas mixture creates sharply non-uniform electric fields around the electrodes. The ionized gas mixture also becomes chemically active. These plasma generation characteristics can be shown by the example array 100. Within each plasma emitter 107, a dielectric tube is formed, between two disk-shaped electrodes 108, 110 of about the same diameter and separated by a small gap, by the through-hole 118 in the dielectric substrate 102. An AC waveform drives a high voltage potential between the two electrodes 108, 110 and a gas mixture, such as helium and oxygen, is flowed through the through-holes 118. When the potential gradient is large enough, the gas mixture within each dielectric tube is ionized and becomes conductive, igniting plasma in the gap between the electrodes 108, 110. A plasma plume is discharged from one end of the dielectric tube (e.g., through an aperture of an electrode 108, 110) and into the surrounding room air. When plasma arrays are operated at atmospheric pressures in air, oxygen and nitrogen molecules are split into single atoms which recombine to form ozone and nitric oxide. The polar nature of oxygen molecule causes a large number of hyperfine resonant frequencies during this process, particularly in the 60 GHz range.

Each cycle of the driving AC waveform initiates a plasma discharge with a velocity that is inversely proportional to its size. At high enough velocities, such as in micro-plasmas, it can induce relativistic effects and create a localized non-homogeneous magnetic field pulse. An array of micro-plasma plumes, such as from an array of plasma emitters 107, provides a large number of mutually coupled pulses which collapse non-linear magnetic fields and separate atoms with higher excitation energy states. This creates localized areas of population inversion.

These areas of high excitation energy due to population inversion create a mechanism for spontaneous emission at the resonance frequencies of oxygen in the 60 GHz range. Spontaneous emission describes when an atom or molecule transitions from an excited energy state to a lower energy state and emits a photon. When an incoming photon of a specific frequency interacts with an electron in an excited energy state, that electron will drop to a lower energy level and transfer its energy to the surrounding electromagnetic field. This creates an additional photon with a phase, frequency, and direction of travel identical to the first photon in a process called stimulated emission. Stimulated emission is the mechanism underlying laser and maser technology.

Figure 2:
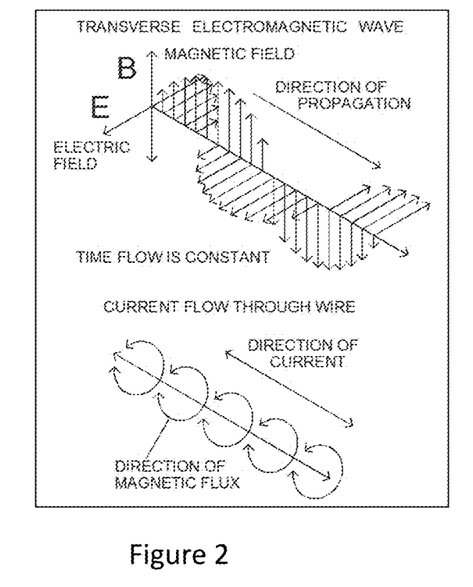
FIG. 2 is an illustration depicting electromagnetic waves.
Figure 3:
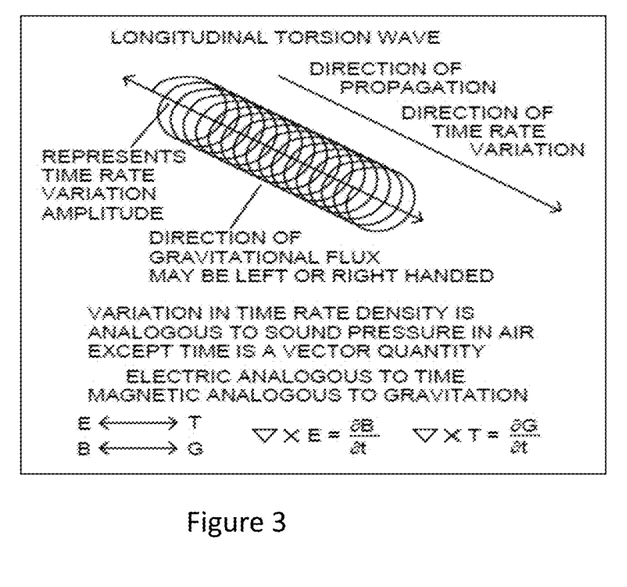
FIG. 3 is an illustration depicting a longitudinal torsion wave.

A previously unexplained repulsive force that is occasionally observed during non-thermal plasma treatment living organisms may point the way to an efficient mechanism for detecting biofield energy. Interactions between torsion waves and the electromagnetic components introduced by plasma and its generation create unique effects that can be used to characterize the biofield. Typically, antennae are used to send and receive information through electromagnetic signals, but torsion waves that comprise the biofield cannot be detected in this manner. This is because, while transverse electromagnetic waves comprise electric and magnetic components that vary within a constant time flow and a constant gravitational force, torsion waves consist of varying temporal and gravitational components that serve as counterparts to the electric and magnetic components of the transverse electromagnetic wave. The comparison of transverse electromagnetic waves and torsion waves is illustrated in FIG. 2 and FIG. 3. As depicted, the electrical component of a transverse electromagnetic wave is analogous to the temporal component of the torsion wave; the magnetic component is analogous to the gravitational component. Small static electric and magnetic components have been detected in torsional waves due to slight non-linearities that may arise in the transport medium, though this leaves a large amount of information in the dynamic components that remains undetected.

The current device detects low-level microwave signals resulting from the unique results of interaction between a biofield and plasma array. Though the torsion waves of a biofield cannot be detected by antennae, they can be detected by an electron avalanche such as occurs in plasma. A side effect of the biofield is a periodic variation in time-rate density, introducing a jitter wherein time speeds up and slows down around a nominal value. In the biofield, this is typically seen at frequencies in the EHF range and higher, such as the resonant frequencies of oxygen. As atoms within a localized area of an electrically conductive plasma are ionized, they collide with and ionize other atoms in a chain reaction known as an electron avalanche. The high potential gradient between two electrodes within the plasma array pulls positively and negatively charged particles (protons and electrons, respectively) of the fluid medium in opposite directions. Electrons, having much less mass than a proton, are accelerated to much higher velocities and may inelastically collide with and ionize other neutral atoms, releasing additional free electrons. Free electrons can be easily captured by neutral molecules rather quickly, however. The ionization and electron avalanche process during plasma generation process occurs in a nanosecond timescale. A change in the time-rate density caused by the biofield will influence electron velocity and hence, momentum during an electron avalanche. Any change in electron momentum will manifest as a change in current during an impact ionization process, since the probability of electron multiplication in a given electron collision will change. This interactive process enables the electron avalanche to be used to detect biofield torsion waves.

Modulation of the electromagnetic signal in this timescale produces a radio carrier signal, as well as side bands of broadband noise from spontaneous emission of particles. When subjected to a plasma array, biological specimens will generate a number of modulated carriers at frequencies centered around the hyperfine resonance frequency of oxygen. Carrier signal could be susceptible to the Zeeman effect, which has been observed in astrophysical masers. The Zeeman effect is observed when a spectral line is split into several components in a static magnetic field. The carrier signals may be modulated by a combination of earth's magnetic field and the associated magnetic fields produced by the non-thermal plasma array interacting with torsional waves. The modulation may impart a circular polarization to the radio waves, a phenomenon in which the electric field of a transverse wave maintains a constant magnitude, but the direction rotates in a right or left circular direction in the plane perpendicular to the direction of wave propagation. Furthermore, interaction between any time varying components of the biofield and the plasma may generate additional carrier signals.

Electromagnetic energy and biofield torsion waves interact when a plasma array is placed near a biological specimen, resulting in microwave energy corresponding to the frequency of time rate variation with the biofield signal. The current disclosure provides a system and method for detecting these microwaves using electron avalanche and circular polarization effects. A microwave antenna, such as a microwave horn or another suitable antenna for receiving and concentrating microwave electromagnetic signals, is placed in the vicinity of the interface between the plasma array and a surface of the biological specimen, which may be a skin surface, a wound, or any other component of the biological specimen. While the array is generating plasma, and optionally also before and after the plasma generation, the horn captures the microwave energy and focuses the microwave energy while delivering it to a custom microwave module with electronic polarization switching. The polarized signal is then passed to a high gain low noise amplifier and harmonic mixer, before being digitized and transferred to a PC. Spectral analysis techniques are then used to analyze the signals. The signals are then characterized by noise temperature versus frequency, comparing signal and noise levels at different points relative to plasma onset and polarization setting. The entire RF bandwidth may be analyzed at the same time, utilizing a number of electronic and computer based hardware to efficiently characterize the carrier signals.

Figure 4:
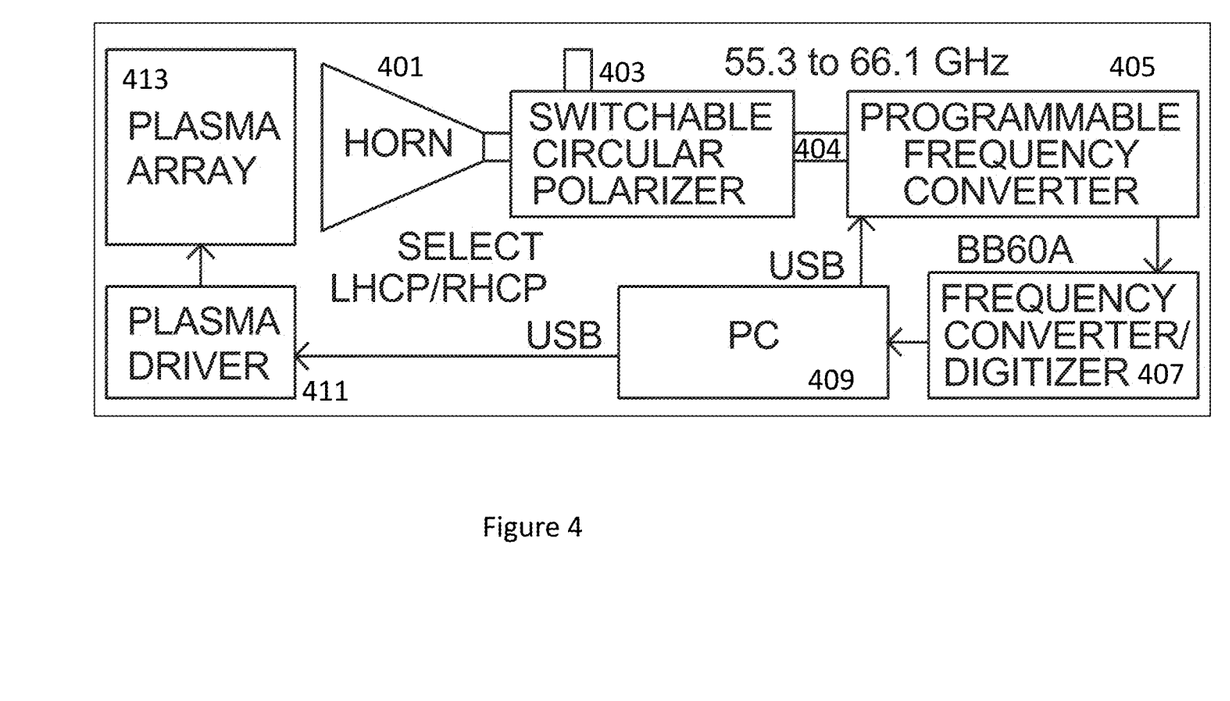
FIG. 4 is a block diagram of the components of the invention

A block diagram of an example embodiment is depicted in FIG. 4. A horn 401 acts as a receiver for carrier signals emanating from an interface space between a plasma array 413 and a biological specimen. This horn 401 may be configured to receive signals across a large range of frequencies, particularly the EHF bands with millimeter wavelengths. The horn 401 transmits signals to linear-to-circular switchable polarizer 403 allowing the polarization to be studied. Biofield torsion waves have a spin characteristic that may impart left-hand or right-hand circular polarization in the microwave radiation emitted by the plasma by measuring and comparing signal levels as the microwave polarizer is switched between left-hand and right-hand circular. A switchable circular polarizer may be selectively changed between right- and left-handed circular or linear polarizations. In some embodiments polarization switching may be manually controlled, though a person skilled in the arts would recognize this could be controlled electronically as well. Measuring and comparing the signal levels as the circular polarizer is switched between modes may be used to detect biofield and microwave interactions. A circular to linear polarization waveguide transition 404 produces a signal that can be read by a programmable frequency converter, 405.

Figure 5:
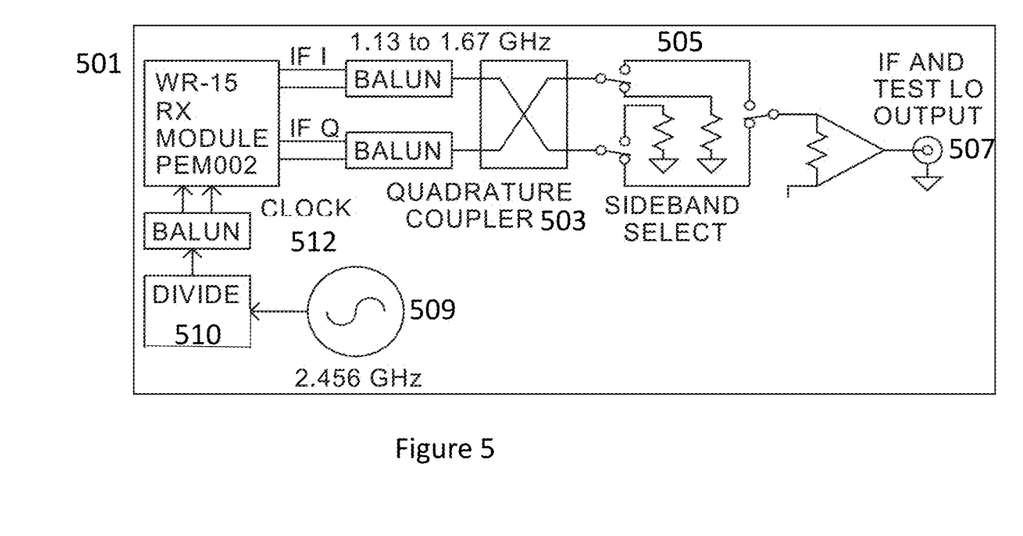
FIG. 5 is a wiring diagram of a programmable frequency converter.

A block diagram of an example embodiment of a programmable frequency converter, such as the frequency converter 405 of FIG. 4, is depicted in FIG. 5. Signals enter the programmable frequency converter through receiver waveguide module 501. In an example embodiment, receiver module 501 is a Silicon Germanium (SiGe) receiver configured for millimeter-wave spectrum allocations. Receiver module 501 utilizes a low noise amplifier to increase the power of carrier waves arising from the interaction of the plasma array and biological specimen, as well as filter any unwanted image frequencies produced by the signal processing. Local oscillator (LO) frequency synthesizer 509 and associated frequency divider 510 generate a reference clock 510 within the receiver, and are used to modulate the frequency of the carrier waves in a heterodyning process, yielding a signal with a lower frequency. A signal from a LO mixes with the carrier waves to yield an intermediate frequency (IF) and a splitting of the waveform into orthogonal I and Q components to allow image rejection using a low IF frequency. The outputs are typically referred to as "I" for "inherent" where the local oscillator has a nominal phase, and "Q" for "quadrature", where the local oscillator phase is shifted 90 degrees. In one embodiment, the frequency reference for the synthesizers inside the programmable frequency converter may be a temperature compensated crystal oscillator to reduce frequency drift with temperature. If the frequency stability is insufficient, an oven stabilized crystal oscillator may be used.

In an example implementation, the frequency of the carrier wave is reduced in a sine wave multiplication or mixing process. For instance, a practical implementation might have a local oscillator running at 17 GHz. This is multiplied by 3, to get a signal at 51 GHz. The 51 GHz signal is fed to a mixer, along with a 59.5 GHz reference signal to produce a 8.5 GHz output signal. An image frequency would also be present at 42.5 GHz. This may be filtered out by a low noise amplifier. The 8.5 GHz IF signal may then be mixed with two 8.5 GHz LO signals, where the two LO signals differ in phase by 90 degrees (i.e.: the I and Q signals described previously). In this implementation, the frequency multiplier and mixer may be combined in the same device.

The I and Q components of the signal act as inputs to a quadrature coupler 503 and an associated switch 505 is used to select between upper and lower IF sidebands. When the I and Q signals are combined in a quadrature combiner, one of the mixing products will increase, since the signals are in phase. The other mixing product will be cancelled, since the signals are out of phase. The quadrature coupler 503 outputs are switched to pass either the high side or low side IF frequency, and reject the opposite sideband. Rejecting one of the sidebands reduces the noise of the signal. The switch 505 in turn is activated by user software and selects which of the IF sidebands to deliver to an output 507 of the frequency converter, by selecting the polarity of the output of the IF quadrature hybrid. The content of the IF output is a frequency-shifted version of the 60 GHz input from radio wave carriers. The internal local oscillator operates over a defined frequency range, and by selecting which sideband to use (upper or lower) enables the device to expand the input frequency range. For example, the IF output 507 covers a limited number of channels; by further splitting the signal with a quadrature coupler 503 and passing only low or high side bands, each with their assigned frequency-channel pairing, the effective number of channels can be increased by switching the LO between the low side and the high side. This extends the usable frequency range of a programmable frequency converter beyond that of a receiver module 501.

Figure 6:
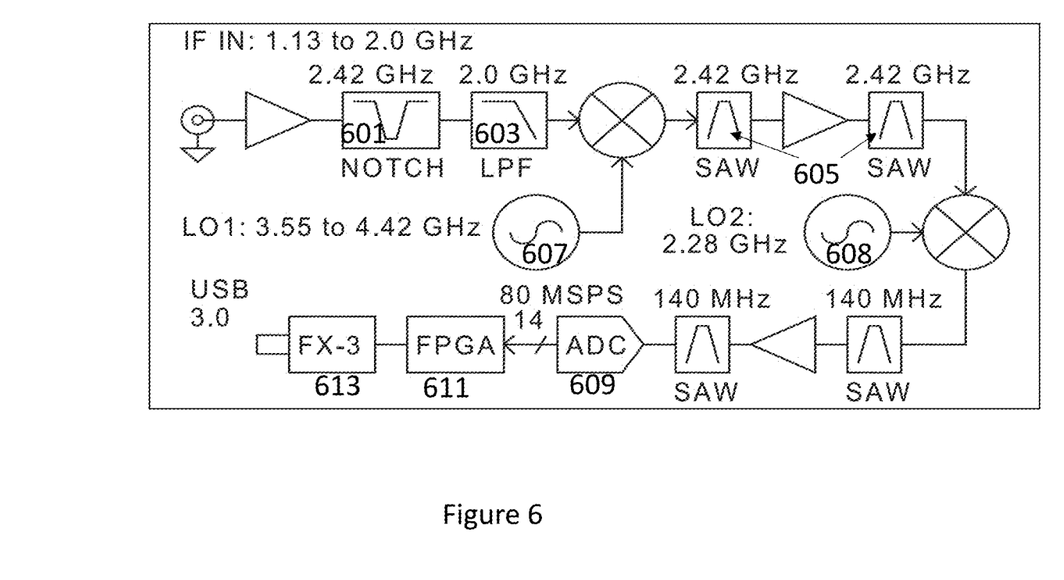
FIG. 6 is a wiring diagram of a spectral analyzer and frequency converter.

Referring again to FIG. 4, IF output from the programmable frequency converter 405 is then connected to a frequency converter/digitizer 407. The frequency converter/digitizer 407 further modulates the IF output from the frequency converter 405 to enable more efficient use of the data and preserve the bandwidth of interest for analysis. Additionally or alternatively, the frequency converter/digitizer 407 may shift the frequency range lower, into the MHz scale, to enable faster and more efficient signal analysis on a CPU 409. An example embodiment of a frequency converter/digitizer 407 is depicted in FIG. 6. The frequency converter/digitizer modulates an input signal frequency using a series of filters that may include notch 601, low-pass 603, and/or saw 605 filters. A frequency converter/digitizer also performs additional heterodyning on the modulated signal using LO frequency synthesizers 607, 608 to shift the frequency range lower, such as into the MHz scale. A frequency converter/digitizer utilizes an analog-to-digital converter 609 to convert the lower frequency signal to a digital signal that may be routed through a field programmable gate array 611 for transfer to a PC. Analog-to-digital conversion may utilize a sample rate high enough to accommodate frequencies in the MHz range. In an example embodiment, a peripheral controller 613 may enable connectivity, such as USB 3.0 functionality, for connecting the device to a PC. Other similar interface systems between FPGA output of the device and a PC may further be utilized in other embodiments.

Referring again to FIG. 4, the signal output from the frequency converter/digitizer 407 may be sent to a hardware computing device, such as a personal computer (PC) 409. Once transferred to a PC 409, the processed signal may undergo further spectral analysis. Spectral analysis may be done by FFT to improve baseband spectrum analysis speed. For example, in one embodiment using a 192 kSPS digitizing sample rate, an FFT size of $N=2^{16}$ creates an equivalent noise bandwidth of 4.4 Hz and requires a plasma on time of about 340 ms. A high performance CPU may be required to accommodate a high data rate of a continuous data stream. In another embodiment, data is digitized in millisecond bursts, timed to retain the phase relationships between the carrier signals for spectral analysis. Digitized data bursts may be optimized to support a practical bandwidth for storage in DRAM, which then may be transferred to a PC at slower rate, such as through an optical transmitter.

In an exemplary embodiment, a harmonic mixer is utilized to improve measurement speed. In a typical embodiment, the harmonic mixer may be driven at 5.8 GHz, and signals could be detected using the $9^{th}$, $10^{th}$ and $11^{th}$ harmonics of a local oscillator. An analog to digital converter sample speed Fs could be 1.5 times the local oscillator frequency, or about 8.7 GSPS. In some embodiments, the ADC sample rate may be too high for real-time signal processing, so a burst of data may be stored, such as in DRAM, while the plasma array is activated and retrieved and processed at a slower rate. Since all microwave signals (in the 60 GHz range) from the plasma are processed at the same time, the phase relationships are preserved. Phase data from subsequent readings can be interpolated to increase frequency resolution or resolve low modulation frequencies. In some embodiments, the high speed FFT may computed in a PC using a GPU card for reduced power consumption.

An FFT will provide amplitude and phase information for each signal, which has been converted in frequency from the 60 GHz range to a range suitable for digitization. An embodiment which analyzes multiple frequencies at the same time using a high digitizer sample rate will provide more information by capturing the instantaneous phase relationships between each signal. A practical embodiment may combine a set of digital down converters with FFT to reduce the total amount of spectrum being analyzed, hence reducing the computing complexity.

The FFT processing increases the speed of the measurement, a benefit over a traditional narrow-band swept measurement. This speed is important in biofield measurement, as the strength of the signal may vary with the physical position of the array relative to the body. The output of the FFT is a frequency spectrum depicting amplitude and phase versus frequency of carrier wave signals.

The spectrum analysis as described may be used to detect amplitude-modulated signals at the resonant maser frequencies of oxygen. This modulation is expected to produce numerous subcarrier waves, which can be characterized by using an appropriate spectrum resolution bandwidth, for example, between 1 Hz and 100 Hz. The plasma array acts as an energy conversion and amplification mechanism when activated. The random plasma discharges from an array manifest as signal noise. However, in proximity to a biofield, the oxygen plasma acts as a maser amplification mechanism for the biofield. This manifests as independent carriers or amplitude spikes during narrow-band spectrum analysis.

Using a spectrum analysis to detect microwave signals from a plasma array in contact with the body (or other biological specimen) may provide useful information about a plasma medicine treatment condition and optimal placement of the plasma array relative to the body.

What is claimed is:

1. A device for detecting and characterizing biofields, the device comprising:
   a microwave horn positionable to, when the microwave horn is placed at an interface between a biological specimen and a plasma array generating atmospheric pressure plasma, receive radio carrier wave signals generated by the plasma interacting with the biological specimen, the microwave horn concentrating the radio carrier wave signals to produce a concentrated radio signal;
   a switchable polarizer in communication with the microwave horn and receiving the concentrated radio signal, the switchable polarizer being reconfigurable in response to an electronic control signal to selectably apply one of a linear polarization, a left-hand circular polarization, and a right-hand circular polarization to the concentrated radio signal to produce a polarized millimeter wave signal;
   a programmable frequency converter in communication with the polarizer and comprising:
      a millimeter-wave spectrum receiver module that receives the polarized millimeter wave signal as input and produces sliding intermediate frequency I/Q signals as output;

a quadrature coupler in communication with the millimeter-wave spectrum receiver module, the coupler receiving the sliding intermediate frequency I/Q signals and combining the sliding intermediate frequency I/Q signals to produce a high sideband intermediate frequency and a low sideband intermediate frequency; and a sideband select switch in communication with the quadrature coupler and configured to receive the high sideband intermediate frequency and the low sideband intermediate frequency and to output a down-sampled intermediate frequency signal selectably comprising the high sideband intermediate frequency or the low sideband intermediate frequency; and a spectrum analyzer in communication with the programmable frequency converter and configured to receive the down-sampled intermediate frequency signal and produce digital output data comprising a frequency spectrum analysis of the down-sampled intermediate frequency signal.

2. The device of claim 1, wherein the millimeter wave receiver module comprises:

a first local oscillator generating a first reference signal at a first frequency;

a first mixer in communication with the first local oscillator and receiving the first reference signal, the first mixer combining the first reference signal with the polarized millimeter wave signal to produce a first intermediate frequency signal;

a low noise amplifier in communication with the first mixer and filtering unwanted image frequencies from the first intermediate frequency signal to produce a filtered first intermediate frequency signal;

a second local oscillator generating a second reference signal at a second frequency; and a second mixer in communication with the low noise amplifier and the second local oscillator and mixing the filtered first intermediate frequency signal with the second reference signal to produce, as the sliding intermediate frequency I/Q signals, an inherent (I) output and a quadrature (Q) output, the phase of the I and Q outputs differing by 90 degrees.

3. The device of claim 2, wherein the spectrum analyzer comprises:

analog filter elements configured to receive the down-sampled intermediate frequency signal and remove unwanted frequency components of the down-sampled intermediate frequency signal to produce a filtered down-sampled intermediate frequency signal;

an analog-to-digital converter (ADC) configured to convert the filtered down-sampled intermediate frequency signal to a digital signal, wherein the sampling frequency of the ADC is greater than the first frequency of the first local oscillator and greater than the second frequency of the second local oscillator;

a dynamic random access memory (DRAM) module in communication with the ADC, the DRAM configured to store the digital signal; and hardware configured to receive the digital signal and perform fast Fourier transform analysis on the digital signal.

4. The device of claim 1, wherein the detector is configured to receive millimeter wave radio signals in a frequency range corresponding to the resonant frequencies of oxygen.

5. The device of claim 1, wherein the switchable polarizer is configured to be electronically switched between applying the linear polarization, the left-hand circular polarization, and the right-hand circular polarization to the concentrated radio signal.

6. The device of claim 1, wherein the programmable frequency converter includes a low pass filter to remove unwanted frequencies below a threshold frequency.

7. The device of claim 1, wherein the spectrum analyzer includes a notch filter to remove specific frequencies from the down-sampled intermediate frequency signal.

8. The device of claim 1, wherein the spectrum analyzer includes a saw filter to remove specific frequencies from the down-sampled intermediate frequency signal.

9. The device of claim 1, wherein the spectrum analyzer includes a local oscillator and mixer, wherein:

the local oscillator is configured to generate a reference signal at a specified frequency band, and the mixer combines the reference signal and the down-sampled intermediate frequency signal to modulate the frequency of the down-sampled intermediate frequency signal.

10. The device of claim 1, wherein the spectrum analyzer includes fast-Fourier transform (FFT) analysis hardware implemented in a field programmable gate array.

11. The device of claim 1, wherein the spectrum analyzer includes fast-Fourier transform (FFT) analysis hardware implemented in an application specific integrated circuit.

12. A method of analyzing multiple radio signals and detecting a biofield torsion wave signal, the method comprising:

positioning a non-thermal plasma array to create an interface between the plasma array and a surface of a biological organism;

generating high frequency millimeter wave radio waves by applying a potential gradient across a first electrode in the non-thermal plasma array and a second electrode in the non-thermal plasma array to generate plasma that interacts with biofield torsion waves emitted at the surface to produce the high frequency millimeter wave radio signals;

receiving the millimeter wave radio signals with a detector, wherein receiving the millimeter wave radio signals comprises positioning a microwave antenna of the detector to receive radio carrier wave signals generated at the interface between the surface of the biological specimen and the plasma array; and causing the detector to produce, from the radio carrier wave signals, a digital output identifying the millimeter wave radio signals, wherein causing the detector to produce the digital output comprises:

utilizing the microwave antenna to concentrate the radio carrier wave signals to produce a concentrated radio signal;

selectably applying one of a linear polarization, a left-hand circular polarization, and a right-hand circular polarization to the concentrated radio signal to produce polarized millimeter wave signals with a switchable polarizer;

converting the polarized millimeter wave signals to a down-sampled intermediate frequency signal, the conversion process comprising:

receiving the polarized millimeter wave signals with a millimeter-wave spectrum receiver module and producing sliding intermediate frequency I/Q signals as output;

receiving the sliding intermediate frequency I/Q signals with a quadrature coupler, combining, with the quadrature coupler, the sliding intermediate frequency I/Q signals into a first mixing product and a second mixing product, wherein the first mixing product is a high sideband intermediate frequency and the second mixing product is a low sideband intermediate frequency; and selecting the high sideband intermediate frequency or the low sideband intermediate frequency as the down-sampled intermediate frequency signal; and converting the down-sampled intermediate frequency signal into a digital signal used to produce the digital output.

13. The method of claim 12, wherein converting the polarized millimeter wave signals to a down-sampled intermediate frequency signal comprises:

generating a first reference signal at a first frequency by a first local oscillator, wherein the first frequency may be multiplied by a first value to modulate the frequency of the reference signal, producing a first intermediate frequency signal by combining the first reference signal with a polarized millimeter wave signal;

filtering any unwanted image frequencies from the first intermediate frequency signal;

generating a second reference signal at a second frequency by a second local oscillator, wherein the second frequency may be multiplied by a second value to modulate the frequency of the second reference signal; and producing two sliding intermediate frequency outputs by combining the second reference signal with the first intermediate frequency signal, wherein the first output is an inherent (I) output and the second output is a quadrature (Q) output and the phase of the I and Q outputs differ by 90 degrees.

14. The method of claim 12, wherein producing the digital output further comprises:

filtering unwanted frequency components of the down-sampled intermediate frequency signal;

converting the filtered down-sampled intermediate frequency signal to the digital signal, storing the digital signal in a dynamic random access memory (DRAM) module, and performing fast Fourier transform analysis on the digital signal.

* * * * *